United States Patent
Iwai et al.

(10) Patent No.: US 9,841,414 B2
(45) Date of Patent: Dec. 12, 2017

(54) AGGREGATED CELL EVALUATION METHOD AND AGGREGATED CELL EVALUATION DEVICE

(71) Applicant: HAMAMATSU PHOTONICS K.K., Hamamatsu-shi, Shizuoka (JP)

(72) Inventors: Hidenao Iwai, Hamamatsu (JP); Takuji Kataoka, Hamamatsu (JP); Satoshi Yamamoto, Hamamatsu (JP); Norikazu Sugiyama, Hamamatsu (JP); Toyohiko Yamauchi, Hamamatsu (JP); Kentaro Goto, Hamamatsu (JP)

(73) Assignee: HAMAMASTU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/766,238

(22) PCT Filed: Feb. 5, 2014

(86) PCT No.: PCT/JP2014/052681
§ 371 (c)(1),
(2) Date: Aug. 6, 2015

(87) PCT Pub. No.: WO2014/123156
PCT Pub. Date: Aug. 14, 2014

(65) Prior Publication Data
US 2015/0369790 A1  Dec. 24, 2015

(30) Foreign Application Priority Data
Feb. 7, 2013 (JP) .................................. 2013-022234

(51) Int. Cl.
*G06K 9/00* (2006.01)
*G01N 33/483* (2006.01)
(Continued)

(52) U.S. Cl.
CPC ......... *G01N 33/4833* (2013.01); *G01B 11/00* (2013.01); *G01N 21/47* (2013.01);
(Continued)

(58) Field of Classification Search
None
See application file for complete search history.

(56) References Cited

U.S. PATENT DOCUMENTS 7,113,817 B1 *  9/2006  Winchester, Jr. .... A61B 3/1233
356/27
7,995,814 B2 *  8/2011  Fingler ................. A61B 3/102
378/4
(Continued)

FOREIGN PATENT DOCUMENTS

JP  2009-276327 A  11/2009
JP  2010-213582 A  9/2010

OTHER PUBLICATIONS

Draijer et al ("Review of laser speckle contrast techniques for visualizing tissue perfusion", 2009).*
(Continued)

*Primary Examiner* — Avinash Yentrapati
(74) *Attorney, Agent, or Firm* — Drinker Biddle & Reath LLP

(57) ABSTRACT

An aggregated cell evaluation apparatus includes a laser light source, a speckle image acquisition unit, an SC calculation unit, an evaluation unit, and a memory unit. The speckle image acquisition unit acquires a two-dimensional speckle image by forward scattered light generated in aggregated cells by irradiation of the aggregated cells with laser light output from the laser light source. The SC calculation unit calculates a speckle contrast value $K_n$ of a speckle image $I_n$ at each time $t_n$, determines a maximum value $K_{max}$ among the speckle contrast values $K_1$ to $K_N$, and normalizes the speckle contrast value $K_n$ at each time $t_n$ by the maxi-
(Continued)

mum value $K_{max}$ to obtain a normalized speckle contrast value $K_n'$. The evaluation unit evaluates motion of the aggregated cells, based on the normalized speckle contrast value $K_n'$ at each time $t_n$.

10 Claims, 3 Drawing Sheets

(51) Int. Cl.
  *G01B 11/00* (2006.01)
  *G01N 21/47* (2006.01)
  *G01N 21/49* (2006.01)
(52) U.S. Cl.
  CPC ..... *G01N 21/49* (2013.01); *G01N 2021/4707* (2013.01); *G01N 2021/479* (2013.01)

(56) References Cited

U.S. PATENT DOCUMENTS

| | | | | |
|---|---|---|---|---|
| 8,760,638 | B2* | 6/2014 | Imai | G01J 3/32 356/32 |
| 8,823,790 | B2* | 9/2014 | Dunn | A61B 5/0059 348/77 |
| 9,226,673 | B2* | 1/2016 | Ferguson, Jr. | A61B 5/0059 |
| 2009/0118622 | A1* | 5/2009 | Durkin | A61B 5/0073 600/473 |
| 2011/0013002 | A1* | 1/2011 | Thompson | A61B 5/0059 348/77 |
| 2011/0034810 | A1* | 2/2011 | Winchester, Jr. | A61B 3/1233 600/476 |
| 2012/0071769 | A1* | 3/2012 | Dunn | A61B 5/0059 600/504 |
| 2012/0095354 | A1* | 4/2012 | Dunn | A61B 5/0261 600/504 |
| 2012/0237104 | A1* | 9/2012 | Fouras | A61B 5/08 382/132 |
| 2012/0307035 | A1* | 12/2012 | Yaqoob | G01B 9/04 348/79 |
| 2013/0088568 | A1* | 4/2013 | Nolte | A61B 5/0075 348/40 |
| 2013/0223705 | A1* | 8/2013 | Ferguson, Jr. | A61B 5/0059 382/128 |
| 2013/0245456 | A1* | 9/2013 | Ferguson, Jr. | A61B 5/0059 600/473 |
| 2013/0275051 | A1* | 10/2013 | Farhat | C12M 41/46 702/19 |
| 2014/0055775 | A1* | 2/2014 | Imai | G01J 3/32 356/73 |
| 2014/0073917 | A1* | 3/2014 | Huang | A61B 5/0066 600/427 |
| 2015/0182136 | A1* | 7/2015 | Durduran | G01B 9/02094 600/425 |
| 2016/0242657 | A1* | 8/2016 | Wang | H04N 5/2353 |

OTHER PUBLICATIONS

English-language translation of International Preliminary Report on Patentability (IPRP) dated Aug. 20, 2015 that issued in WO Patent Application No. PCT/JP2014/052681.
Ruri Chihara, "The Role of Rho Kinase: Third Kinase System in the Regulation of Excitation-Contraction Coupling of Cardiac Muscle", J Saitama Med School, vol. 31, No. 2, 2004, p. 103-p. 113.
T. Hayakawa et al., "Noninvasive Evaluation of Contractile Behavior of Cardiomyocite Monolayers Based on Motion Vector Analysis", Tissue Engineering Part C, vol. 18, No. 1, 2012, p. 21-p. 32.
D. W. Peterson et al., "Decreased Myocardial Contractility in Papillary Muscles from Atherosclerotic Rabbits", Circ Res. 45(3), 1979, p. 338-p. 346.
Manabu Tominaga et al., "Observation of biological tissue activity by speckle method under optical microscope", Proceedings of 40th Symposium on Stress-strain Measurement and Strength Evaluation, 2009, p. 5-p. 8.
Moy, Austin, J., et al., "Wide-field functional imaging of blood flow and hemoglobin oxygen saturation in the rodent dorsal window chamber," Microvascular Research, Academic Press, US, vol. 82, No. 3, Jul. 8, 2011, pp. 199-209, XP028106945.
Braga, Roberto, A., et al., "Live biospeckle laser imaging of root tissues," European Biophysics Journal; With Biophysics Letters, Springer, Berlin, DE, vol. 38, No. 5, Mar. 6, 2009, pp. 679-686, XP019705331.
Liu, Qian, et al., "Laser speckle contrast imaging: monitoring blood flow dynamics and vascular structure of photodynamic therapy," Proceedings of the SPIE—The International Society for Optical Engineering SPIE—The International Society for Optical Engineering USA, vol. 5630, No. 1, Jan. 18, 2005, pp. 26-33, XP40196320.
An, Ran, et al., "Live tissue viability and chemosensitivity assays using digital holographic motility contrast imaging," Applied Optics, Optical Society of America, DC; US, vol. 52, No. 1, Jan. 1, 2013, pp. A300-A309, XP001580234.
Bazulev, N, et al., "Laser monitor for soft and hard biotissue analysis using dynamic speckle photography," Laser Physics, Moscow, RU, vol. 13, No. 5, May 1, 2003, pp. 786-795, XP009101662.
Boas, David, A., et al., "Laser speckle contrast imaging in biomedical optics," Journal of Biomedical Optics, vol. 15, No. 1, Jan. 1, 2010, p. 011109, XP55304160.

* cited by examiner

AGGREGATED CELL EVALUATION METHOD AND AGGREGATED CELL EVALUATION DEVICE

TECHNICAL FIELD

The present invention relates to an aggregated cell evaluation method and an aggregated cell evaluation apparatus.

BACKGROUND ART

The conventional evaluation of cardiac muscle cells was carried out, for example, in such a manner that cardiac muscle cells were isolated and extracted from a cardiac organ of a laboratory animal, they were cultured on a laboratory dish or the like to prepare primary cultured cells, and the primary cultured cells were used to evaluate the cardiac muscle cells. During the primary culture, cells grow horizontally in a monolayer state (in a sheet shape) in a certain period and the cardiac muscle cells come to beat (contract and relax) in synchronization. However, such primary cultured cells are not human cells and thus are not suitable for use in evaluation of cardiotoxicity or the like on human cardiac muscle cells because of the difference of species.

In recent years, with progress of technologies to culture stem cells such as iPS cells or ES cells, it became feasible to artificially create aggregated cells being a three-dimensional aggregate of cells and evaluation of the aggregated cells (e.g., evaluation of change of the aggregated cells upon administration of a drug) has been becoming important. To conduct evaluation of drug efficacy using the cardiac muscle cells prepared from human iPS cells or human ES cells as a specimen is extremely important in evaluation of drug efficacy and safety because it can be done by use of cells of human origin. A cardiac muscle tissue, which is a three-dimensional aggregate of cardiac muscle cells created from human iPS cells or human ES cells, is a tissue in which not only the cardiac muscle cells but also fibroblast cells and others for holding the peripheries of the cells are cultured in mixture, and thus it is feasible to perform the evaluation under a condition similar to a human heart.

Here, Non Patent Document 1 suggests the evaluation method for sheet-shaped cells being a two-dimensional aggregate of cells. Since the sheet-shaped cardiac muscle is obtained by sampling the cardiac muscle cells nearly 100% and culturing them, the evaluation of the sheet-shaped cardiac muscle is evaluation in a state different from the real heart. Further, since the sheet-shaped cells adhere individually to a base plate such as the bottom of a laboratory dish, the adhesion inhibits change in motion to be caused by drug effect and thus such cells do not allow accurate evaluation of motion.

In contrast to it, aggregated cells are less affected by the inhibition effect as to motion of cells located in regions away from the base plate, though motion of cells near the base plate is inhibited by adhesion to the base plate. Therefore, the aggregated cells allow more accurate evaluation of motion than the sheet-shaped cells, and are more likely to physiologically reflect the change in motion to be caused by drug effect, the aggregated cells are thus in a favorable state for evaluation of cardiotoxicity or the like in drug discovery.

CITATION LIST

Non Patent Literature

Non Patent Document 1: Hayakawa T, "Noninvasive evaluation of contractile behavior of cardiomyocyte monolayers based on motion vector analysis", Tissue Engineering Part C, Vol. 18, No. 1, pp. 21-32, 2012

Non Patent Document 2: Peterson D W, Griffith D W Jr, Napolitano C A., "Decreased myocardial contractility in papillary muscles from atherosclerotic rabbits", Circ Res, 1979 September; 45(3), pp. 338-346

Non Patent Document 3: Ruri Chihara, "The Role of Rho Kinase: Third Kinase System in the Regulation of Excitation—Contraction Coupling of Cardiac Muscle" J Saitama Med School Vol, 31 No, 2 Apr. 2004 pp. 103-113

SUMMARY OF INVENTION

Technical Problem

The method described in Non Patent Document 1 is intended for evaluation of the sheet-shaped cells in two-dimensional motion, and it is difficult to apply it to evaluation of aggregated cells in three-dimensional motion.

The present invention has been accomplished in order to solve the above problem, and it is an object of the present invention to provide a method and an apparatus capable of readily evaluating the motion of aggregated cells.

Solution to Problem

An aggregated cell evaluation method of the present invention comprises: (1) a speckle image acquisition step of irradiating aggregated cells with laser light to capture speckle images by forward scattered light generated in the aggregated cells by irradiation with the laser light, at respective times $t_1$ to $t_N$ in time series; (2) an SC calculation step of calculating a speckle contrast value $K_n$ of the speckle image at each time $t_n$ out of the times $t_1$ to $t_N$ acquired in the speckle image acquisition step, determining a maximum value $K_{max}$ among the speckle contrast values $K_1$ to $K_N$, and normalizing each speckle contrast value $K_n$ by the maximum value $K_{max}$ to obtain a normalized speckle contrast value $K_n'$; and (3) an evaluation step of evaluating motion of the aggregated cells, based on the normalized speckle contrast value $K_n'$ at each time $t_n$ obtained in the SC calculation step or based on a correlation time; or a speed $V_n$ obtained therefrom.

An aggregated cell evaluation apparatus of the present invention comprises: (1) a laser light source for outputting laser light; (2) a speckle image acquisition unit for capturing speckle images by forward scattered light generated in aggregated cells by irradiation of the aggregated cells with the laser light output from the laser light source, at respective times $t_1$ to $t_N$ in time series; (3) an SC calculation unit for calculating a speckle contrast value $K_n$ of the speckle image at each time $t_n$ out of the times $t_1$ to $t_N$ acquired by the speckle image acquisition unit, determining a maximum value $K_{max}$ among the speckle contrast values $K_1$ to $K_N$, and normalizing each speckle contrast value $K_n$ by the maximum value $K_{max}$ to obtain a normalized speckle contrast value $K_n'$; and (4) an evaluation unit for evaluating motion of the aggregated cells, based on the normalized speckle contrast value $K_n'$ at each time $t_n$ obtained by the SC calculation unit or based on a correlation time $\tau_n$ or a speed $V_n$ obtained therefrom.

Advantageous Effects of Invention

The present invention has made it feasible to readily evaluate the motion of aggregated cells.

DESCRIPTION OF EMBODIMENTS

An embodiment of the present invention will be described below in detail with reference to the accompanying drawings. In the description of the drawings the same elements will be denoted by the same reference symbols, without redundant description.

Figure 1:
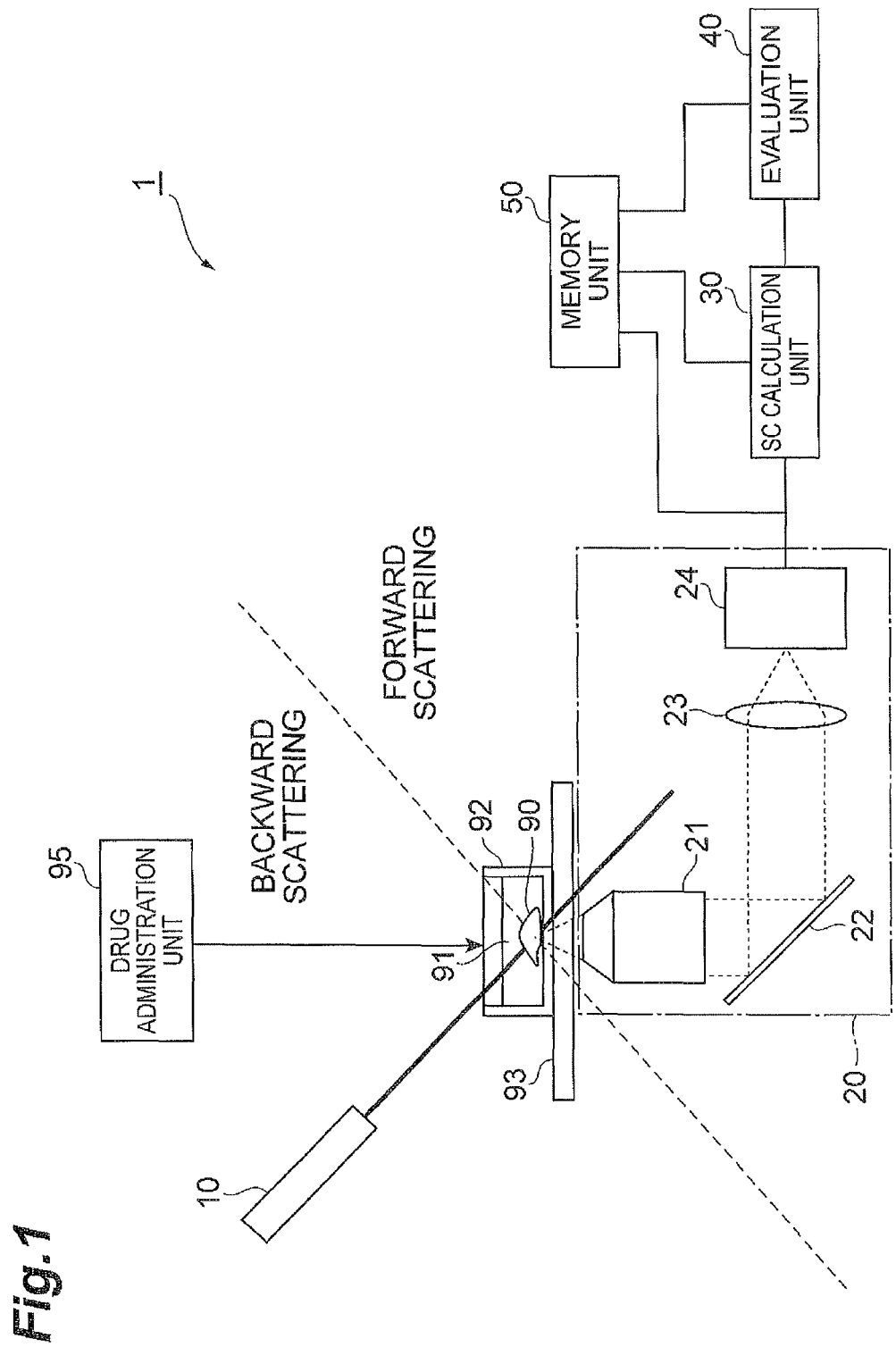
FIG. 1 is a drawing showing a configuration of an aggregated cell evaluation apparatus 1 according to an embodiment.

FIG. 1 is a drawing showing the configuration of the aggregated cell evaluation apparatus 1 of the present embodiment. FIG. 1 shows a configuration of an inverted microscope. The aggregated cell evaluation apparatus 1 includes a laser light source 10, a speckle image acquisition unit 20, an SC calculation unit 30, an evaluation unit 40, and a memory unit 50. The aggregated cell evaluation apparatus 1 is an apparatus that evaluates motion of aggregated cells 90 being a three-dimensional aggregate of cells. The aggregated cells 90, together with a culture medium 91, are put in a laboratory dish 92, and this laboratory dish 92 is placed on a stage 93. The aggregated cells 90 are, for example, a cardiac muscle tissue which is a three-dimensional aggregate of cardiac muscle cells created from human iPS cells or human ES cells. The cardiac muscle tissue is a tissue in which not only the cardiac muscle cells but also fibroblast cells and others are cultured in mixture.

The laser light source 10 is provided above the stage 93. The laser light source 10 outputs laser light to irradiate the aggregated cells 90 in the laboratory dish 92 with the laser light. The laser light source 10 to be used herein can be any laser light source. The laser light output from the laser light source 10 may be applied to the aggregated cells 90 after its beam diameter is increased by a beam expander.

The speckle image acquisition unit 20 acquires a two-dimensional speckle image by forward scattered light generated in the aggregated cells 90 by irradiation of the aggregated cells 90 with the laser light output from the laser light source 10. The speckle image acquisition unit 20 acquires such speckle images at respective times $t_1$ to $t_N$ in time series. The speckle image acquisition unit 20 includes an objective lens 21, a mirror 22, an imaging lens 23, and an image pickup unit 24.

The objective lens 21 is provided below the stage 93. The objective lens 21 receives the forward scattered light generated in the aggregated cells 90 by irradiation of the aggregated cells 90 with the laser light output from the laser light source 10. This forward scattered light travels via the objective lens 21, mirror 22, and imaging lens 23 to reach an imaging plane of the image pickup unit 24. The image pickup unit 24 is configured, for example, by a CCD camera or a CMOS camera.

An angle between the direction of incidence of the laser light to the aggregated cells 90 and the optical axis direction of the objective lens 21 is preferably appropriately set so as to prevent light not scattered by the aggregated cells 90 out of the laser light output from the laser light source 10, from entering the objective lens 21. This setup allows the imaging plane of the image pickup unit 24 to receive light consisting primarily of the forward scattered light generated in the aggregated cells 90, thereby enabling acquisition of clear speckle images.

The evaluation apparatus 1 may have, instead of the configuration of the inverted microscope, a configuration of an upright microscope. In the latter case, the laser light source 10 is disposed below the stage 93 and the objective lens 21 above the stage 93.

The aggregated cells 90 are a three-dimensional aggregate of cells each having the size of about 10 μm and have the total size of several hundred μm. When the whole aggregated cells 90 are desired to be observed, the magnification of the objective lens 21 is preferably low enough to secure an observation field. The magnification of the objective lens 21 is, for example, 4× or 10×. In another case, where the whole aggregated cells 90 cannot fall within the image field, a partial region of the aggregated cells 90 may be set in the image field.

The aggregated cells 90 have the thickness in the optical axis direction of the objective lens 21 and cannot fit in the depth of focus of the objective lens 21 in some cases. However, speckle images have a property of being formed not only on the focal plane but also on any plane off the focal plane, and positions in the optical axis direction of the objective lens 21 is not significant. It is sufficient that the focal plane of the objective lens 21 be located inside the aggregated cells 90.

An exposure time for acquisition of each speckle image by the speckle image acquisition unit 20 affects contrast of the speckle image of the aggregated cells 90 in motion and thus is preferably set to an appropriate duration of time in the range of about 1 ms to 30 ms to allow acquisition of clear speckle images. In the present embodiment, the exposure time is an important parameter. The major reason for variation in speckle contrast due to motion of a specimen is that the light intensity of a speckle image repetitively becomes bright and dark in the exposure time in conjunction with the motion of the specimen whereby the intensity is averaged in terms of time. Therefore, there is no variation in speckle contrast if the exposure time is sufficiently short with respect to the motion of the specimen. On the other hand, there is no variation in speckle contrast if the exposure time is sufficiently long with respect to the motion of the specimen. Therefore, the exposure time needs to be set to an appropriate duration of time.

In the case of the cardiac muscle and papillary muscle of animals, according to Non Patent Documents 2 and 3, the time to arrival at a contraction peak is approximately 200 to 400 msec and the time necessary for relaxation approximately 400 to 800 msec. When evaluation of drug efficacy to strengthen or weaken pulsation is considered, it is necessary to assume the speeds ranging from approximately one tenth to ten times the foregoing ranges, and thus the time range to be taken into consideration in analysis of contraction and relaxation is from 20 to 8000 msec. However, the beat rate differs depending upon species, e.g., between animals and a human, and therefore the time range for analysis of contraction and relaxation should be further expanded; it is considered herein that the time range to be taken into consideration is from 1 to 10000 msec.

The exposure time $\Delta t$ should be considered in view of the following two conditions. The first condition is that the exposure time $\Delta t$ needs to satisfy $f_S > f_B$, where $f_B$ represents the frequency of heart beats of the cardiac muscle tissue and $f_S$ the frame rate (Hz) of the camera. At frame rates of the camera not satisfying this relational expression, it is impossible to separate speeds in contraction and relaxation of the cardiac muscle tissue. Since there is the relation of $f_S<1/\Delta t$ between the frame rate $f_S$ of the camera and the exposure time $\Delta t$, the exposure time $\Delta t$ satisfying $f_S>f_B$ can be determined.

The second condition is that, in conjunction with the sampling theorem, a phase change amount $(2\pi/\lambda)V\Delta t$ of light due to speed change needs at least to be not more than $\pi$, where V represents a speed of motion of the cardiac muscle tissue and $\Delta$ an exposure time by which a speckle image is obtained without blur. Namely, it is necessary to satisfy the condition of $\Delta t<\lambda/V$. For example, when the illumination light used is HeNe laser light with the center wavelength of 0.633 µm and the speed of the cardiac muscle tissue is V=10µ/s, the exposure time is estimated to be about $\Delta t=63$ ms. In practice the preferred exposure time is a value ranging from a half to one tenth of the thus-obtained value.

The foregoing appropriate exposure time may be determined as follows: images are taken once with a sufficiently short exposure time (or at a sufficiently fast frame rate) for blur-less imaging of speckle images generated from a moving object, the time-series speckle images are stored in a memory of a computer, an adequate number of frames are then accumulated on the computer, and, based thereon the exposure time is adjusted to a quasi-appropriate value.

The speckle contrast varies depending upon the exposure time. Therefore, when a speed is quantitatively determined from speckle contrasts, it is preferable to normalize speckle contrast values by the exposure time T. It is noted that if the exposure time is sufficiently short with respect to the motion of the specimen or if the exposure time is sufficiently long with respect to the motion of the specimen, an accurate speed cannot be obtained even with the normalization of speckle contrast values by the exposure time T.

The memory unit 50 stores a speckle image $I_n(x, y)$ acquired at each time $t_n$ out of times $t_1$ to $t_N$ by the speckle image acquisition unit 20. x, y are coordinate values indicating a position in a two-dimensional speckle image, and when the image pickup unit 24 has a two-dimensional pixel structure as in the case of a CCD, x, y are coordinate values indicating a pixel position. The memory unit 50 also stores the result obtained by the SC calculation unit 30 as described below.

The SC calculation unit 30 calculates a speckle contrast value $K_n$ of the speckle image $I_n$ at each time $t_n$ stored by the memory unit 50. The SC calculation unit 30 determines a maximum value $K_{max}$ among these speckle contrast values $K_1$ to $K_N$. The SC calculation unit 30 normalizes the speckle contrast value K each time $t_n$ by the maximum value $K_{max}$ to obtain a normalized speckle contrast value $K_n'$. Then the evaluation unit 40 evaluates the motion of the aggregated cells 90, based on the normalized speckle contrast value $K_n'$ at each time $t_n$ obtained by the SC calculation unit 30.

Here, there is mutual dependence among the three parameters, the normalized speckle contrast value $K_n'$ at each time $t_n$, correlation time $\tau_n$, and speed $V_n$, as described below. Therefore, the evaluation of the motion of the aggregated cells 90 may be made based on any one of the normalized speckle contrast value $K_n'$ at each time $t_n$, correlation time $\tau_n$, and speed $V_n$.

The apparatus is preferably provided with a drug administration means, as schematically illustrated by a drug administration unit 95 in FIG. 1. This drug administration means administers a drug to the aggregated cells 90 prior to or in the middle of the acquisition of speckle images by the speckle image acquisition unit 20. At this time, the evaluation unit 40 evaluates influence of the drug administered by the drug administration means on the aggregated cells 90, based on the evaluation result of the motion of the aggregated cells 90.

The aggregated cell evaluation method of the present embodiment can be carried out with use of the aggregated cell evaluation apparatus 1. The aggregated cell evaluation method of the present embodiment includes a speckle image acquisition step, an SC calculation step, and an evaluation step which are carried out in order.

In the speckle image acquisition step, the laser light source 10 irradiates the aggregated cells 90 with the laser light. Then the speckle image acquisition unit 20 acquires speckle images by forward scattered light generated in the aggregated cells 90 by the irradiation with the laser light, at respective times $t_1$ to $t_N$ in time series. The speckle image $I_n(x, y)$ acquired at each time $t_n$ is stored in the memory unit 50.

In the SC calculation step, the SC calculation unit 30 calculates the speckle contrast value $K_n$ of the speckle image at each time $t_n$, determines the maximum value $K_{max}$ among these speckle contrast values $K_1$ to $K_N$, and normalizes the speckle contrast value $K_n$ at each time $t_n$ by the maximum value $K_{max}$ to obtain the normalized speckle contrast value $K_n'$. In the evaluation step, the evaluation unit 40 then evaluates the motion of the aggregated cells, based on the normalized speckle contrast value $K_n'$ at each time $t_n$.

The method preferably further comprises a drug administration step of administering a drug to the aggregated cells 90 by the drug administration means prior to or in the middle of the speckle image acquisition step. In this case, the evaluation step is configured so that the evaluation unit 40 evaluates the influence of the drug on the aggregated cells, based on the evaluation result of the motion of the aggregated cells.

Next, the contents of the respective processes by the SC calculation unit 30 and the evaluation unit 40 (the respective processes of the speckle image acquisition step and the SC calculation step) will be described in more detail.

First, a mean value $I_{mean}$ and a standard deviation $\sigma$ are determined from intensities of $(2W+1)^2$ pixels in a region with a window size $2W+1$ centered at each position (x, y) of the speckle image $I_n(x, y)$. The speckle contrast value $K_n$ at each position (x, y) is calculated from these mean value $I_{mean}$ and standard deviation a by the following formula (1). The speckle contrast value $K_n$ is determined for all pixels of the speckle image $I_n(x, y)$ at each time $t_n$, thereby calculating a speckle contrast image $K_n(x, y)$ for the speckle image $I_n(x, y)$.

[Math 1]

$$K_n(x, y) = \frac{\sigma}{I_{mean}} \quad (1)$$

A mean value (mean speckle contrast value) $K_{n\_mean}$ is calculated from the speckle contrast values of all the pixels in the speckle contrast image $K_n(x, y)$ at each time $t_n$. A maximum value $K_{max}$ is determined among the N mean speckle contrast values $K_{1\_mean}$ to $K_{N\_mean}$. Then the mean speckle contrast value $K_{n\_mean}$ at each time $t_n$ is normalized by the maximum value $K_{max}$ to obtain the normalized speckle contrast value $K_n'(=K_{n\_mean}/K_{max})$.

The reason for this normalization is as follows. Namely, it is known that, theoretically, the contrast value is 1 for a fully developed speckle obtained from a still specimen under an ideal condition. It is also known that speckle contrast values are generally not more than 1. On the other hand, actual conditions even with the specimen at a standstill are different from the ideal condition. In practice, there are cases where contrast values of speckles obtained from the still specimen are not 1, for example, because of stray light or coherence length of laser light. This difference between the theoretical value and the actually measured value would raise a problem in the evaluation of motion of the specimen. Therefore, the normalization as described above is carried out.

Then, the correlation time $\tau_n$ is determined from the normalized speckle contrast value $K_n'$ at each time $t_n$ by the following formula (2) and the speed $V_n$ is determined from the correlation time $\tau_n$ at each time $t_n$ by the following formula (3). It is noted that T represents the exposure time in acquisition of each speckle image and $\lambda$ the wavelength of the laser light. There are also known relational expressions other than the formula (2) as relations between the speckle contrast value and correlation time.

[Math 2]

$$K_n' = \sqrt{\frac{\tau_n}{2T}\left(1 - \exp\left(-\frac{2T}{\tau_n}\right)\right)} \quad (2)$$

[Math 3]

$$V_n = \frac{\lambda}{2\pi\tau_n} \quad (3)$$

The arithmetic operation to determine the mean speckle contrast value $K_{n\_mean}$ from the speckle contrast image $K_n(x, y)$ at each time $t_n$ may be performed after the formula (2). In that case, a mean correlation time $\tau_{n\_mean}$ is calculated from a correlation time image $\tau_n(x, y)$. Furthermore, the above mean calculation may be performed after the formula (3) and in this case, a speed image $V_n(x, y)$ is obtained from the correlation time image $\tau_n(x, y)$ and thereafter a mean speed $V_n$ may be calculated.

The SC calculation unit 30 may divide the resultant speckle image $I_n(x, y)$ into a plurality of segment images $I_n^{(m)}$ each including an appropriate number of pixels. In this case, subsequently, $K_n$, $K_n'$, $\tau_n$, and speed $V_n$ are calculated for each of the segment images $I_n^{(m)}$ to obtain two-dimensional mapping images of these parameters to evaluate the motion of the aggregated cells 90. It is noted that m in $I_n^{(m)}$ represents a segment number.

As indicated by the formula (2) and the formula (3), there is mutual dependence among the three values of the normalized speckle contrast value $K_n'$, the correlation time $\tau_n$, and the speed $V_n$ at each time $t_n$. Therefore, the normalized speckle contrast value $K_n'$, the correlation time $\tau_n$ and the speed $V_n$ at each time t all are equivalent in the evaluation of the motion of the aggregated cells 90, and can be used each as an index for the evaluation of the motion of the aggregated cells 90.

Example 1

Next, the below will describe an example of the aggregated cell evaluation apparatus and aggregated cell evaluation method of the present embodiment. In the present example, the aggregated cells 90 as an evaluation object were a cardiac muscle tissue in the size of about 600 μm. The laser light source 10 was a HeNe laser light source to output the laser light at the wavelength of 633 nm. The magnification of the objective lens 21 was 10×. The image pickup unit 24 was a CCD camera having the number of pixels of 512×512 and the size of one pixel was 16×16 μm. The exposure time in imaging by the image pickup unit 24 was 10 ms and the frame rate 100 fps.

Figure 2:
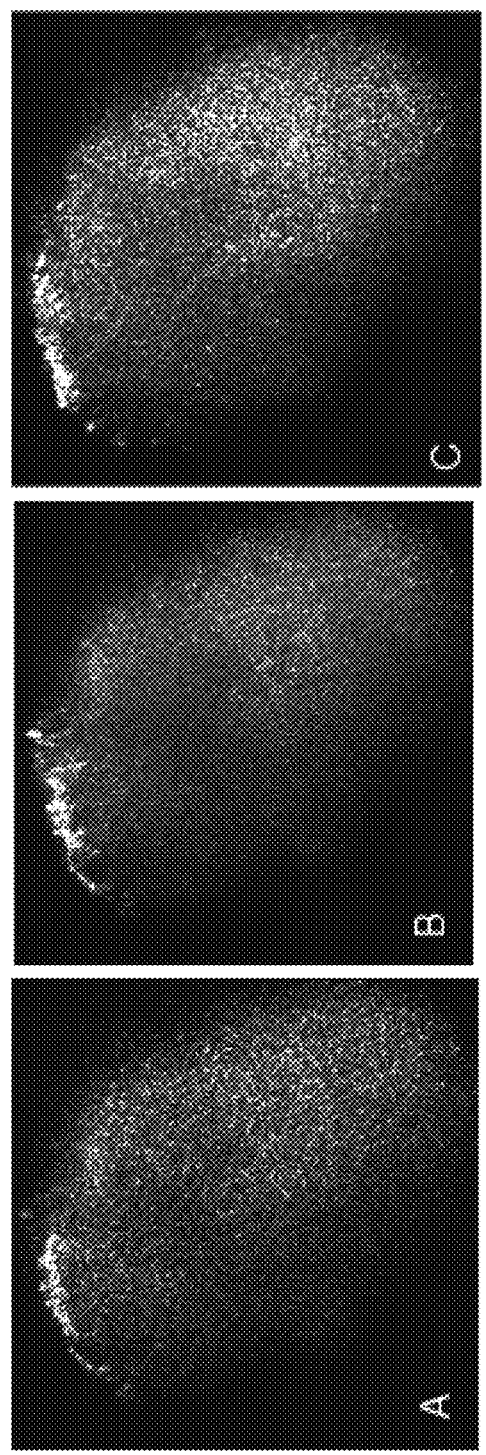
FIG. 2 includes photographs of speckle images acquired in an example.

FIG. 2 includes photographs of speckle images acquired in the present example. The size of the field of view of each of the speckle images A to C shown in FIG. 2 is 0.82×0.82 μm. The speckle image A is an image of the cardiac muscle tissue in a stop period. The speckle image B is an image of the cardiac muscle tissue in a contraction period. The speckle image C is an image of the cardiac muscle tissue in a relaxation period.

In the speckle image A of the cardiac muscle tissue in the stop period, a speckle pattern (bright-/dark-spot pattern) is clearly observed. In contrast to it, the speckle image B of the cardiac muscle tissue in the contraction period demonstrates reduction in the speckle pattern. The speckle pattern shows repetitions of brightness and darkness in conjunction with beats (expansion and contraction) of the cardiac muscle tissue. Since the speckle pattern becomes repetitively bright and dark sufficiently quickly with respect to the exposure time, the speckle pattern looks blurred in the speckle image B of the cardiac muscle tissue in the contraction period and, in other words, it suffers degradation of contrast. In this manner, there is correlation between the contrast of the speckle pattern and the speed of motion of the specimen. Based on this correlation, the correlation time $\tau_n$ can be determined from the speckle contrast $K_n'$ and the speed $V_n$ can be further determined.

Figure 3:
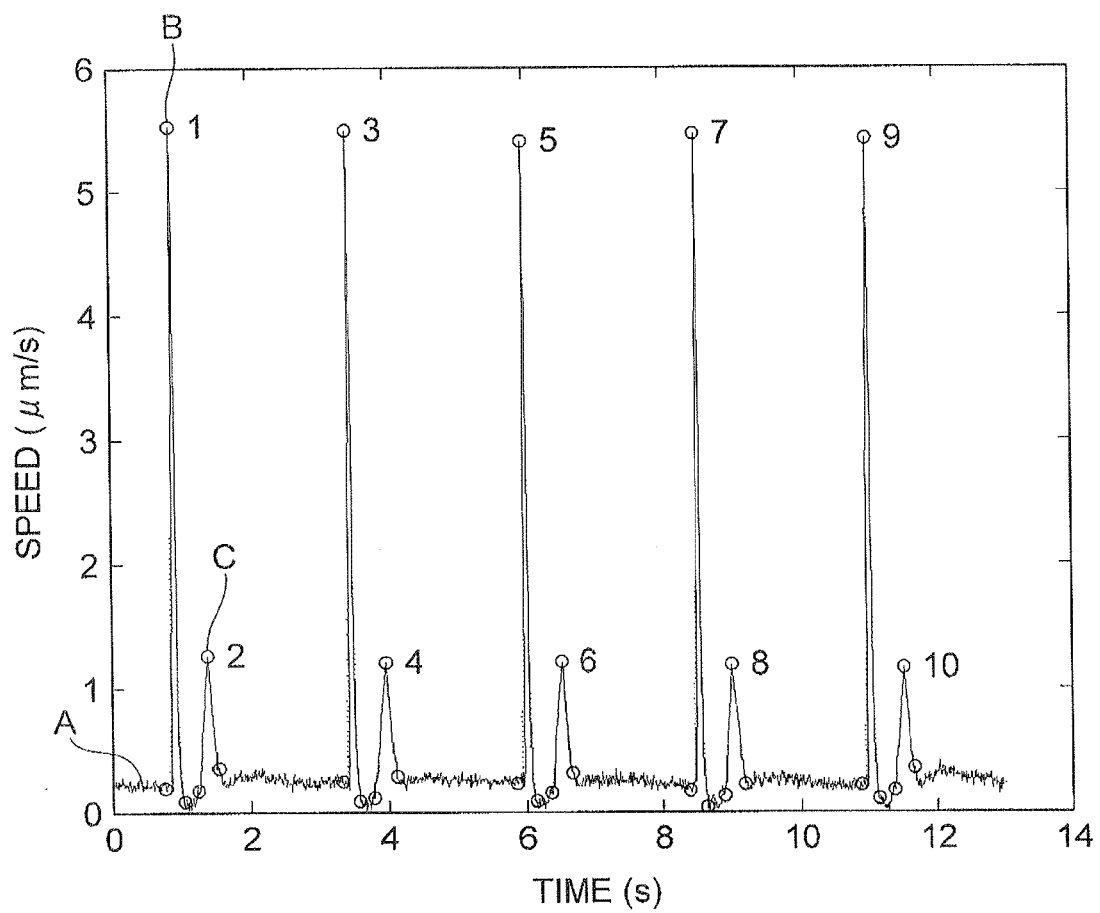
FIG. 3 is a graph showing speeds $V_n$ at respective times $t_n$ obtained in an example.

FIG. 3 is a graph showing the speed $V_n$ at each time $t_n$ obtained in the present example. In FIG. 3, peaks 1, 3, 5, 7, and 9 indicate the speeds in maximum acceleration during contraction periods of the cardiac muscle tissue, and peaks 2, 4, 6, 8, and 10 the speeds in maximum acceleration during relaxation periods of the cardiac muscle tissue. The times when the respective speckle images A to C in FIG. 2 were acquired are indicated by A to C in FIG. 3. From this FIG. 3, the motion of the cardiac muscle tissue (e.g., intervals of appearance of the respective peaks, magnitudes of the peaks in the contraction periods, magnitudes of the peaks in the relaxation periods, and differences or ratios between the respective magnitudes of the peaks in the contraction periods and the peaks in the relaxation periods) can be evaluated. Furthermore, influence of a drug on the cardiac muscle tissue can be evaluated based on the evaluation result of the motion of the cardiac muscle tissue.

The aggregated cell evaluation method and aggregated cell evaluation apparatus according to the present invention are not limited to the above-described embodiment and configuration examples but can be modified in many ways.

The aggregated cell evaluation method according to the above embodiment is configured to comprise: (1) a speckle image acquisition step of irradiating aggregated cells with laser light to capture speckle images generated by forward scattered light generated in the aggregated cells by irradiation with the laser light, at respective times $t_1$ to $t_N$ in time series; (2) an SC calculation step of calculating a speckle contrast value $K_n$ of the speckle image at each time $t_n$ out of the times $t_1$ to $t_N$ acquired in the speckle image acquisition step, determining a maximum value $K_{max}$ among the speckle contrast values $K_1$ to $K_N$, and normalizing each speckle contrast value $K_n$ by the maximum value $K_{max}$ to obtain a normalized speckle contrast value $K_n'$; and (3) an evaluation step of evaluating motion of the aggregated cells, based on the normalized speckle contrast value $K_n'$ at each time $t_n$ obtained in the SC calculation step or based on a correlation time $\tau_n$ or a speed $V_n$ obtained therefrom.

The aggregated cell evaluation apparatus according to the above embodiment is configured to comprise: (1) a laser light source for outputting laser light; (2) a speckle image acquisition unit for capturing speckle images generated by forward scattered light generated in aggregated cells by irradiation of the aggregated cells with the laser light output from the laser light source, at respective times $t_1$ to $t_N$ in time series; (3) an SC calculation unit for calculating a speckle contrast value $K_n$ of the speckle image at each time $t_n$ out of the times $t_1$ to $t_N$ acquired by the speckle image acquisition unit, determining a maximum value $K_{max}$ among the speckle contrast values $K_1$ to $K_N$, and normalizing each speckle contrast value $K_n$ by the maximum value $K_n$, to obtain a normalized speckle contrast value $K_n'$; and (4) an evaluation unit for evaluating motion of the aggregated cells, based on the normalized speckle contrast value $K_n'$ at each time $t_n$ obtained by the SC calculation unit or based on a con-elation time $\tau_n$ or a speed $V_n$ obtained therefrom.

The aggregated cell evaluation method of the above configuration preferably further comprises; a drug administration step of administering a drug to the aggregated cells prior to or in the middle of the speckle image acquisition step, and in this case, the evaluation step preferably comprises evaluating influence of the drug on the aggregated cells, based on the evaluation result of the motion of the aggregated cells.

The aggregated cell evaluation apparatus of the above configuration preferably further comprises: drug administration means for administering a drug to the aggregated cells prior to or in the middle of acquisition of the speckle images by the speckle image acquisition unit, and in this case, the evaluation unit preferably evaluates influence of the drug on the aggregated cells, based on the evaluation result of the motion of the aggregated cells.

In the aggregated cell evaluation method of the above configuration, the SC calculation step preferably comprises dividing the speckle image at each time t, into a plurality of segment images each including a plurality of pixels, and calculating the speckle contrast value $K_n$ for each of the segment images. In the aggregated cell evaluation apparatus of the above configuration, the SC calculation unit preferably divides the speckle image at each time $t_n$ into a plurality of segment images each including a plurality of pixels, and calculates the speckle contrast value $K_n$ for each of the segment images. In this case, thereafter, $K_n'$, $\tau_n$, and speed $V_n$ are calculated for each of the segment images to obtain two-dimensional mapping images of these parameters, and the motion of the aggregated cells is evaluated based thereon.

INDUSTRIAL APPLICABILITY

The present invention is applicable as a method and an apparatus capable of readily evaluating the motion of aggregated cells.

REFERENCE SIGNS LIST

1—aggregated cell evaluation apparatus, 10—laser light source, 20—speckle image acquisition unit, 21—objective lens, 22—mirror, 23—imaging lens, 24—image pickup unit, 30—SC calculation unit, 40—evaluation unit, 50—memory unit, 90—aggregated cells, 91—culture medium, 92—laboratory dish, 93—stage.

The invention claimed is:
1. An aggregated cell evaluation method comprising:
irradiating aggregated cells with laser light and capturing speckle images generated by forward scattered light generated in the aggregated cells by irradiation with the laser light, with a set exposure time and at respective times $t_1$ to $t_N$ in time series, the aggregated cells being a three-dimensional aggregate of cells with beating;
calculating a speckle contrast value $K_n$ of the speckle image with the set exposure time at each time $t_n$ out of the times $t_1$ to $t_N$ acquired in the speckle image acquisition step, determining a maximum value $K_{max}$ among the speckle contrast values $K_1$ to $K_N$, and normalizing each speckle contrast value $K_n$ by the maximum value $K_{max}$ to obtain a normalized speckle contrast value $K_n'$; and
evaluating motion of the aggregated cells, based on the normalized speckle contrast value $K_n'$ at each time $t_n$ or based on a correlation time $\tau_n$ or a speed $V_n$ obtained therefrom.

2. The aggregated cell evaluation method according to claim 1, further comprising:
administering a drug to the aggregated cells prior to or during speckle image capture; and
evaluating influence of the drug on the aggregated cells based on an evaluation result of the motion of the aggregated cells.

3. The aggregated cell evaluation method according to claim 1, wherein the speckle contrast value $K_n$ is obtained by:
dividing the speckle image at each time $t_n$ into a plurality of segment images each including a plurality of pixels; and
calculating the speckle contrast value $K_n$ for each of the segment images.

4. An aggregated cell evaluation apparatus comprising:
a laser light source configured to output laser light;
a speckle image acquisition unit including a light detector and configured to capture speckle images generated by forward scattered light generated in aggregated cells by irradiation of the aggregated cells with the laser light output from the laser light source, with a set exposure time and at respective times $t_1$ to $t_N$ in time series, the aggregated cells being a three-dimensional aggregate of cells with beating;
a machine-readable non-transitory memory; and
one or more processors communicatively coupled to the memory and configured to read instructions from the memory which, when executed by the one or more processors, cause the apparatus to perform operations comprising:
calculating a speckle contrast value $K_n$ of the speckle image with the set exposure time at each time $t_n$ out of the times $t_1$ to $t_N$ acquired by the speckle image acquisition unit, determine a maximum value $K_{max}$ among the speckle contrast values $K_1$ to $K_N$, and normalize each speckle contrast value $K_n$ by the maximum value $K_{max}$ to obtain a normalized speckle contrast value $K_n'$; and
evaluating motion of the aggregated cells, based on the normalized speckle contrast value $K_n'$ at each time $t_n$ or based on a correlation time $\tau_n$ or a speed $V_n$ obtained therefrom.

5. The aggregated cell evaluation apparatus according to claim 4, wherein the operations further comprise:

evaluating influence of a drug on the aggregated cells based on an evaluation result of the motion of the aggregated cells.

6. The aggregated cell evaluation apparatus according to claim 4, wherein the speckle contrast value $K_n$ is obtained by operations comprising:
dividing the speckle image at each time $t_n$ into a plurality of segment images each including a plurality of pixels; and
calculating the speckle contrast value $K_n$ for each of the segment images.

7. The aggregated cell evaluation method according to claim 1, wherein the cells with beating are cardiac muscle cells, and the aggregated cells are a cardiac muscle tissue being the three-dimensional aggregate of the cardiac muscle cells.

8. The aggregated cell evaluation method according to claim 7, wherein the speckle images are captured by a camera, and the set exposure time satisfies $f_S > f_B$, where $f_B$ represents a frequency of heart beats of the cardiac muscle tissue, and $f_S$ represents a frame rate of the camera.

9. The aggregated cell evaluation apparatus according to claim 4, wherein the cells with beating are cardiac muscle cells, and the aggregated cells are a cardiac muscle tissue being the three-dimensional aggregate of the cardiac muscle cells.

10. The aggregated cell evaluation apparatus according to claim 9, wherein the light detector included in the speckle image acquisition unit is a camera, and the set exposure time satisfies $f_S > f_B$, where $f_B$ represents a frequency of heart beats of the cardiac muscle tissue, and $f_S$ represents a frame rate of the camera.

* * * * *

UNITED STATES PATENT AND TRADEMARK OFFICE
CERTIFICATE OF CORRECTION

PATENT NO. : 9,841,414 B2
APPLICATION NO. : 14/766238
DATED : December 12, 2017
INVENTOR(S) : Hidenao Iwai et al.

It is certified that error appears in the above-identified patent and that said Letters Patent is hereby corrected as shown below:

On the Title Page

In Item (73) "Assignee" change "HAMAMASTU PHOTONICS K.K." to --"HAMAMATSU PHOTONICS K.K.--

Signed and Sealed this
Thirteenth Day of March, 2018

Andrei Iancu
*Director of the United States Patent and Trademark Office*